US009842252B2

(12) United States Patent
Edgerton et al.

(10) Patent No.: US 9,842,252 B2
(45) Date of Patent: Dec. 12, 2017

(54) SYSTEMS AND METHODS FOR USE IN CHARACTERIZING AGRICULTURAL PRODUCTS

(75) Inventors: Michael D. Edgerton, St. Louis, MO (US); Pradip K. Das, Olivette, MO (US); Troy W. Hobbs, O'Fallon, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 1276 days.

(21) Appl. No.: 12/788,853

(22) Filed: May 27, 2010

(65) Prior Publication Data

US 2010/0329515 A1    Dec. 30, 2010

Related U.S. Application Data

(60) Provisional application No. 61/182,523, filed on May 29, 2009.

(51) Int. Cl.
*G01N 21/85* (2006.01)
*A01H 1/00* (2006.01)
(Continued)

(52) U.S. Cl.
CPC ............ *G06K 9/00496* (2013.01); *C12P 7/06* (2013.01); *G01N 21/359* (2013.01);
(Continued)

(58) Field of Classification Search
CPC ............. C12P 7/06; Y02E 50/17; Y02E 50/16
See application file for complete search history.

(56) References Cited

U.S. PATENT DOCUMENTS 3,675,769 A    7/1972    Story
3,852,914 A    12/1974   Levengood
(Continued)

FOREIGN PATENT DOCUMENTS

CL    1035-03    5/2003
CL    673-03     2/2004
(Continued)

OTHER PUBLICATIONS

Delta "Pioneer evaluates hybrids for ethanol", Sep. 3, 2004, Delta Farm Press, available at http://deltafarmpress.com/pioneer-evaluates-hybrids-ethanol.*
(Continued)

*Primary Examiner* — Robert Yamasaki
*Assistant Examiner* — Charles Zoltan Constantine
(74) *Attorney, Agent, or Firm* — James E. Davis; Harness, Dickey & Pierce, P.L.C.

(57) ABSTRACT

A method is provided for use in optimizing ethanol yield from agricultural products. The method includes imaging agricultural products to determine predicted ethanol yields for the agricultural products and assigning characterizations to the imaged agricultural products based on their predicted ethanol yields. An apparatus is provided for collecting, retaining, and/or transporting bulk quantities of agricultural products. The apparatus includes an analyzer configured to image the agricultural products for use in determining the predicted ethanol yields. And, a system is provided for tracking and/or monitoring agricultural products. The system includes an analyzer configured to image the agricultural products for use in determining the predicted ethanol yields, a central processor configured to communicate with the analyzer to thereby link the imaged agricultural products with their predicted ethanol yields, and a telecommunications link coupling the analyzer to the central processor for
(Continued)

allowing the communication between the analyzer and the central processor.

24 Claims, 9 Drawing Sheets

(51) Int. Cl.
| | | |
|---|---|---|
| C12P 7/06 | (2006.01) | |
| G06K 9/00 | (2006.01) | |
| G01N 21/359 | (2014.01) | |
| G01N 21/3563 | (2014.01) | |
| G01N 21/35 | (2014.01) | |

(52) U.S. Cl.
CPC ......... *G01N 21/3563* (2013.01); *G01N 21/85* (2013.01); *A01H 1/00* (2013.01); *G01N 2021/3595* (2013.01); *G01N 2021/8592* (2013.01); *Y02E 50/16* (2013.01); *Y02E 50/17* (2013.01)

(56) References Cited

U.S. PATENT DOCUMENTS

| | | | |
|---|---|---|---|
| 3,861,788 A | 1/1975 | Webster | |
| 4,037,476 A * | 7/1977 | McCrabb | 73/864.31 |
| 4,037,970 A | 7/1977 | Webster et al. | |
| 4,040,747 A | 8/1977 | Webster | |
| 4,204,950 A | 5/1980 | Burford, Jr. | |
| 4,225,242 A | 9/1980 | Lane | |
| 4,260,262 A | 4/1981 | Webster | |
| 4,278,183 A | 7/1981 | Billington | |
| 4,568,644 A | 2/1986 | Wang et al. | |
| 4,696,308 A | 9/1987 | Meller et al. | |
| 4,713,781 A | 12/1987 | Brizgis et al. | |
| 4,734,584 A | 3/1988 | Rosenthal | |
| 4,752,689 A | 6/1988 | Satake et al. | |
| 4,946,046 A | 8/1990 | Affleck et al. | |
| 5,021,662 A | 6/1991 | Johnson | |
| 5,132,538 A | 7/1992 | Norris | |
| 5,475,221 A | 12/1995 | Wang | |
| 5,480,354 A | 1/1996 | Sadjadi | |
| 5,533,145 A | 7/1996 | Shofner et al. | |
| 5,616,851 A | 4/1997 | McMahon et al. | |
| 5,628,830 A | 5/1997 | Brink | |
| 5,668,374 A | 9/1997 | DiFoggio et al. | |
| 5,751,421 A | 5/1998 | Wright et al. | |
| 5,916,780 A | 6/1999 | Foody et al. | |
| 5,918,977 A | 7/1999 | Borggaard et al. | |
| 5,920,018 A | 7/1999 | Wilkerson et al. | |
| 5,957,773 A | 9/1999 | Olmsted et al. | |
| 5,959,102 A | 9/1999 | Wasserman et al. | |
| 5,987,384 A | 11/1999 | Matson | |
| 5,991,025 A | 11/1999 | Wright et al. | |
| 6,009,186 A | 12/1999 | Gorretta et al. | |
| 6,100,526 A | 8/2000 | Mayes | |
| 6,115,115 A | 9/2000 | Skarie et al. | |
| 6,118,055 A | 9/2000 | Livesey | |
| 6,155,103 A | 12/2000 | Diekhans et al. | |
| 6,185,990 B1 | 2/2001 | Missotten et al. | |
| 6,327,569 B1 | 12/2001 | Reep | |
| 6,366,681 B1 | 4/2002 | Hutchins | |
| 6,418,805 B1 | 7/2002 | Carney et al. | |
| 6,421,990 B1 | 7/2002 | Ohlemeyer et al. | |
| 6,449,932 B1 | 9/2002 | Cooper et al. | |
| 6,483,583 B1 | 11/2002 | Wright et al. | |
| 6,509,180 B1 | 1/2003 | Verser et al. | |
| 6,537,826 B1 | 3/2003 | Horigane | |
| 6,559,655 B1 | 5/2003 | Rosenthal et al. | |
| 6,566,125 B2 | 5/2003 | Johnston et al. | |
| 6,624,888 B2 | 9/2003 | Panigrahi et al. | |
| 6,646,264 B1 | 11/2003 | Modiano et al. | |
| 6,706,989 B2 | 3/2004 | Hunter et al. | |
| 6,749,810 B2 | 6/2004 | Carr et al. | |
| 6,791,683 B2 | 9/2004 | Sjodin | |

| | | | |
|---|---|---|---|
| 6,809,819 B1 | 10/2004 | Vinjamoori et al. | |
| 6,845,326 B1 | 1/2005 | Panigrahi et al. | |
| 6,848,243 B2 | 2/2005 | Carr et al. | |
| 6,851,662 B2 | 2/2005 | Panigrahi et al. | |
| 6,947,144 B2 | 9/2005 | Kim et al. | |
| 7,044,306 B2 | 5/2006 | Deppermann | |
| 7,074,125 B2 | 7/2006 | Ho et al. | |
| 7,123,750 B2 | 10/2006 | Lu et al. | |
| 7,169,040 B2 | 1/2007 | Kormann et al. | |
| 7,189,160 B2 | 3/2007 | Pirro | |
| 7,215,420 B2 | 5/2007 | Gellerman et al. | |
| 7,265,831 B2 | 9/2007 | Kormann et al. | |
| 7,367,155 B2 | 5/2008 | Kotyk et al. | |
| 7,403,855 B2 | 7/2008 | Fuessley et al. | |
| 7,502,113 B2 | 3/2009 | Deppermann et al. | |
| 7,600,642 B2 | 10/2009 | Deppermann | |
| 7,630,848 B2 | 12/2009 | Loosme | |
| 7,673,572 B2 | 3/2010 | Deppermann et al. | |
| 7,775,167 B2 | 8/2010 | Stehling et al. | |
| 7,830,504 B2 | 11/2010 | Deppermann et al. | |
| 2001/0014750 A1 | 8/2001 | Ulrich et al. | |
| 2001/0024796 A1 | 9/2001 | Selifonov et al. | |
| 2003/0063276 A1 | 4/2003 | Sjodin | |
| 2003/0066277 A1 | 4/2003 | Behnke | |
| 2003/0224496 A1 | 12/2003 | Jakel et al. | |
| 2004/0021862 A1 | 2/2004 | Panigrahi et al. | |
| 2004/0091888 A1 | 5/2004 | Nishio et al. | |
| 2004/0130714 A1 | 7/2004 | Gellerman et al. | |
| 2004/0187459 A1 | 9/2004 | Carr et al. | |
| 2005/0082207 A1 | 4/2005 | Deppermann | |
| 2005/0097021 A1 | 5/2005 | Behr et al. | |
| 2005/0132685 A1 | 6/2005 | Carr et al. | |
| 2005/0150202 A1 | 7/2005 | Quick | |
| 2005/0154221 A1 | 7/2005 | Lysenko et al. | |
| 2006/0027750 A1 | 2/2006 | Kormann et al. | |
| 2006/0042527 A1 | 3/2006 | Deppermann | |
| 2006/0042528 A1 | 3/2006 | Deppermann | |
| 2006/0093522 A1 | 5/2006 | Kormann et al. | |
| 2007/0048872 A1 | 3/2007 | Deppermann et al. | |
| 2007/0204366 A1 | 8/2007 | Deppermann et al. | |
| 2007/0207485 A1 | 9/2007 | Deppermann et al. | |
| 2007/0240241 A1 | 10/2007 | Ubach et al. | |
| 2007/0240242 A1 * | 10/2007 | Modiano et al. | 800/284 |
| 2008/0113367 A1 | 5/2008 | Becker et al. | |
| 2008/0131254 A1 | 6/2008 | Cope et al. | |
| 2008/0131924 A1 | 6/2008 | Cope et al. | |
| 2008/0203201 A1 | 8/2008 | Deppermann et al. | |
| 2008/0243392 A1 | 10/2008 | Fuessley et al. | |
| 2008/0310674 A1 | 12/2008 | Modiano et al. | |
| 2008/0317279 A1 | 12/2008 | Deppermann et al. | |
| 2009/0075325 A1 | 3/2009 | Das et al. | |

FOREIGN PATENT DOCUMENTS

| | | |
|---|---|---|
| CL | 2190-05 | 5/2007 |
| DE | 10048643 | 5/2001 |
| DE | 10236515 | 9/2003 |
| DE | 102006002437 | 7/2007 |
| EP | 0539537 B2 | 5/1993 |
| EP | 0636310 A1 | 2/1995 |
| EP | 0511184 B1 | 6/1998 |
| EP | 1053671 B1 | 11/2000 |
| GB | 1151988 A2 | 5/1969 |
| GB | 1471076 | 4/1977 |
| JP | 9072847 | 3/1997 |
| SU | 1658858 | 6/1991 |
| WO | WO 96/24830 | 8/1996 |
| WO | WO 98/14046 A1 | 4/1998 |
| WO | WO 98/44140 | 10/1998 |
| WO | WO 99/00425 | 1/1999 |
| WO | WO 99/40419 | 8/1999 |
| WO | WO 9946971 A1 | 9/1999 |
| WO | WO 00/42838 | 7/2000 |
| WO | WO 00/71993 A1 | 11/2000 |
| WO | WO 01/23884 A1 | 4/2001 |
| WO | WO 01/89288 A1 | 11/2001 |
| WO | WO 01/94608 | 12/2001 |
| WO | WO 02/077608 A2 | 10/2002 |
| WO | WO 03/084847 | 10/2003 |

(56) References Cited

FOREIGN PATENT DOCUMENTS

| WO | WO 03/100381 | 12/2003 |
|---|---|---|
| WO | WO 2004/039946 A2 | 5/2004 |
| WO | WO 2004/063333 | 7/2004 |
| WO | WO 2006/026466 A2 | 3/2006 |
| WO | WO 2006/026467 A2 | 3/2006 |
| WO | WO 2006/086792 | 8/2006 |
| WO | WO 2007/025250 A2 | 3/2007 |
| WO | WO 2008/103609 A1 | 8/2008 |
| ZA | 200006949 | 11/2007 |

OTHER PUBLICATIONS

Naidu "Effects of Ground Corn Particle Size on Ethanol Yield and This Stillage Soluble Solids" Cereal Chem. 2007, 84(1) 6-9.*

Adams et al, *Matrix Assisted Laser Desorption Ionization Time of Flight Mass Spectrometry Analysis of Zeins in Mature Maize Kernels*, J. Agric. Food Chem., 52: 1842-49 (2004).

Archibald et al., "Development of Short-Wavelength Near-Infrared Spectral Imaging for Grain Color Classification," SPIE vol. 3543, 1998, pp. 189-198.

Bietz et al, in Wrigley (Ed.), *Identification of Food-Grain Varieties*, American Association of Cereal Chemists, St. Paul, 73-90 (1995).

Bietz, *Separation of Cereal Proteins by Reversed-Phase High-Performance Liquid Chromatography*, Journal of Chromatography, 255: 219-238 (1983).

Bothast RJ, Schlicher MA. (2005) Biotechnological processes for conversion of corn into ethanol. Appl Microbiol Biotechnol. 67(1): 19-25.

Brennan et al., Journal of Cereal Science 24, *Structural Differences in the Mature Endosperms of Good and Poor Malting Barley Cultivars*, (1996) pp. 171-177.

Brumback et al., *Automating Fatty Acid Analysis from Seeds: From Field Samples to Data Bases*, Laboratory Automation & Information Management, Elsevier Science Publishers BV., Amsterdam, NL, vol. 21, No. 2/3, pp. 215-222 (1993).

Cabrera et al., Open Storage of Soybean Seed in Mississippi, Mississippi Agricultural and Forestry Experiment Station, Sep. 2002. <http://msucares.com/pubs/techbulletins/tb204.htm>.

Campbell MR, Brumm TJ, Glover DV, (1997) Whole grain amylase analysis in maize using near-infrared transmittance spectroscopy. Cereal Chem. 74(3): 300-303.

Campbell MR, Mannis SR, Port A, Zimmerman AM, Glover DV. (1999) Prediction of starch amylase content versus total grain amylase content in corn by near-infrared transmittance spectroscopy. Cereal Chem. 76:552-557.

Cober, Elroy R. et al.; May 1, 2005; *Genetic improvement rates of short-season soybean increase with plant population*; Crop Science, No. 3, vol. 45, p. 1029.

Coleman et al., The Maize y-Zein Sequesters α-Zein and Stabilizes Its Accumulation in Protein Bodies of Transgenic Tobacco Endosperm, The Plant Cell, vol. 8, pp. 2335-2345 (Dec. 1996).

Daun et al., "Comparison of Three Whole Seed Near-Infrared Analyzers for Measuring Quality Components of Canola Seed", vol. 71, No. 10, Jul. 1994, pp. 1063-1068.

Delwiche, "Single Wheat Kernel Analysis by Near-Infrared Transmittance: Protein Content," Analytical Techniques and Instrumentation, vol. 72, No. 1, 1995, pp. 11-16.

Dien et al, *Fate of Bt Protein and Influence of Corn Hybrid on Ethanol Production*, Cereal Chemistry, 79(4): 582-585 (2002).

Dombrink-Kurtzman, *Examination of Opaque Mutants of Maize by Reversed-Phase High-Performance Liquid Chromatography and Scanning Electron Microscopy*, Journal of Cereal Science, 19: 57-64 (1994).

Dowell et al., "Automated Single Wheat Kernel Quality Measurement Using Near-Infrared Reflectance," ASAE Annual International Meeting, 1997, paper No. 973022.

Dowell, "Automated Color Classification of Single Wheat Kernels Using Visible and Near-Infrared Reflectance," Cereal Chemistry, vol. 75(1), 1998, pp. 142-144.

DowJones Newswires; Sep. 7, 1999; *Textron, Case Corp Unveil Continuous-Flow Grain Analyzer*; DowJones Newswires.

Dr. Jolanta Soos, "Industrial Process Monitoring Requires Rugged AOTF Tools", Laser Focus World, Aug. 1994.

Drummond, S., Joshi, A. & Sudduth, K.A., Application of Neural Networks: Precision Farming. In 1998 IEEE International Joint Conference on Neural Networks, vol. 1, 211-215 (IEEE, 1998).

Fang et al., *Neural Network Modeling of Physical Properties of Ground Wheat*, Cereal Chemistry, 75(2)251-253 (1998).

Fiber Optics Weekly Update; Dec. 24, 2004; *Fiber-optic sensors help farmers find high-quality wheat; SENSORS; Brief Article*; Fiber Optics Weekly Update, No. 51, vol. 24, p. 5.

Fjeldheim, Brad; Aug. 14, 2005; *Area farmers market new grain analyzer*; The Billings Gazette, p. D1.

Fox et al., *Relations of Grain Proximate Composition and Physical Properties to Wet-Milling Characteristics of Maize*, Cereal Chemistry, 69(2):191-197 (1992).

Frizzi, Analysis of zeins in mature wild-type and transgenic maize kernels by Matrix-Assisted-laser-Desorption ionization time-of-flight mass spectrometry (MALDI-TOF MS), $47^{th}$ Annual Maize genetics conference, Mar. 10-13, 2005 p. 1,42 (p. 1-2).

Gillespie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.

Hagge, Don; Jan. 1, 2005; *Evaluating NIR for precision agriculture grain harvest: design and development of a Grain Quality Monitor is the next logical step*; Implement & Tractor, No. 1, vol. 120, p. 25.

Hi-Bred International, Inc., Downloadable Photos—Laser-Assisted Seed Selection, <http://www.pioneer.com/web/site/portal/menuiteam.b9e99dcb8e2cfd8ecfe6d10093a0/>, printed as of Nov. 25, 2008, 4 pages.

*Identification of monosodium glutamate by visible and near infrared reflectance spectroscopym* Qiu, Z.; Mao, J.; Shao, Y.; Li, X.; He, Y. Coll. of Biosystems Eng. & Food Sci., Zhejiang Univ., Hangzhou (Abstract), (paper appears in: Signal Processing, The 8th International Conference on Publication Date: 16-20, 2006); http://ieeexplore.ieee.org/xpl/freeabs_all.jsp?arnumber=4128816.

Infratec 1241 Grain Analyzer, FOSS, http://www.foss.us/Solutions/ProductsDirect/{/media/files/Solutions/DataSheets/Infratec1241GrainAnalyzer/99991677e%20pdf.ashx>, retrieved on Apr. 23, 2010, 2 pages.

J.P. Hazebroek et al., Analysis of Genetically Modified Oils, Progress in Lipid Research 39 (2000) pp. 477-506.

Just-food.com; Dec. 21, 2004; *USA: New optical sensors help detect high-quality wheat*; Just-Food.

Kincade, Kathy; Feb. 1, 2005; *Optical sensor checks wheat quality in real time; Spectroscopy*, Laser Focus World, No. 2, vol. 41, p. 40.

Kotyk et al., High-Throughput Determination of Oil Content in Corn Kernels Using Nuclear Magnetic Resonance Imaging, JAOCS, vol. 82, No. 12, 2005, pp. 855-862.

Kramer et al., *Transgenic Avidin Maize is Resistant to Storage Insect Pests*, Nature Biotechnology, vol. 18, Jun. 2000, pp. 670-674.

Krysan, Breakthrough Technologies, Ice-Cap. A High-Throughput Method for Capturing Plant Tissue Samples for Genotype Analysis, Plant Physiology, Jul. 2004 vol. 135, pp. 1162-1169.

Lee K-M, Herrman TJ, Bean SR, Jackson DS, Lingenfelser J. (2007) Classification of dry-milled maize grit yield groups using quadratic discriminant analysis and decision tree algorithm. Cereal Chem. 84:152-161.

Lueschen et al., *Agronomic Practices for Production of Ethanol from Sweet Sorghum*, Journal of Production Agriculture, vol. 4, No. 4, pp. 619-625 (1991).

M2 Presswire; Dec. 17, 2004; *US ARS: Optical sensors help farmers find high-quality wheat*; M2 Presswire.

Massie and Norris, "Spectral Reflectance and Transmittance Properties of Grain in the Visible and Near Infrared", Transactions of the ASAE, Winter Meeting of the American Society of Agricultural Engineers, 1965, pp. 598-600.

Morrison, *Sampling in Seed Health Testing*, The American Physiopathology, 1999, 89: 1084-1087.

(56) References Cited

OTHER PUBLICATIONS

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.
Paulsen MR, Singh M. (2004) Calibration of near-infrared transmission grain analyzer for extractable starch in maize. Biosystems Engineering 89:79-83.
Philippeau et al, *Influence of Grain Source on Ruminal Characteristics and Rate, Site, and Extent of Digestion in Beef Steers*, Journal of Animal Science, 77:1587-1596 (1999).
Powell, Joy; Oct. 6, 2002; *New agriculture takes root; by harvesting information technology, farmers are bringing digital precision to their fields*; Star Tribune, p. 1D.
PR Newswire, Monsanto Collaborates with Foss to Develop Analytical Tools for Soybeans, Installs Improved Low-Linolenic Calibration System for 2007 Fall Harvest, Sep. 20, 2007, 3 pages.
Rapid Identification of Organic Contaminants in Retreated Waste Water Using AOTF near-IR Spectrometry, *ISA 1995 Meeting Proceedings*, pp. 87-95, 1995.
Robutti, "Maize Kernel Hardness Estimation in Breeding by Near-Infrared Transmission Analysis," Analytical Techniques and Instrumentation vol. 72, No. 6, 1995, pp. 632-636.
Roggenbuck, R.M. Applications of Precision Agriculture to Ethanol Production. Master's Thesis, University of Minnesota (2004). 33 page excerpt of Chapter 3 (pp. 47-79), with 1 page of front matter and 1 page of library index record.
Scharf, P.C. et al.; Nov. 1, 2002; *Remote sensing for nitrogen management*; Journal of Soil and Water Conservation, No. 6, vol. 57, p. 518.
Serial Extraction of Endosperm Drillings (SEED)—A Method for Detecting Transgenes and Proteins in Single Viable Maize Kernels, Varaporn Sangton, et al., Plant Molecular Biology Reporter 19: 151-158, Jun. 2001, International Society for Plant Molecular Biology.
Singh M, Paulsen MR, Tian L, Yao H. (2005) Site-specific study of corn oil, protein, and extractable starch variability using NIT spectroscopy. Appl. Engin. Agric. 21:239-251.
Singh et al., *Compositional, Physical, and Wet-Milling Properties of Accessions Used in Germplasm Enhancement of Maize Project*, Cereal Chemistry, 78(3):330-335 (2001).
Smith et al., Genetic Purity and Testing Technologies for Seed Quality: A Company Perspective, Seed Science Research, 1998, vol. 8, pp. 285-293.
Southwest Farm Press; Jan. 13, 2005; *Optical sensors help farmers find high-quality wheat*; Southwest Farm Press, p. 23.
Soybean Cyst Nematode, Plant Pathology, Iowa State University, University Extension, Ames, Iowa, Pm-879, Revised Oct. 1995, 6 pages.
Subramanyam et al., *Corn and Sorghum. 2. Effect of Grain Maturity on Nutritional Quality*, Nutrition Reports International, vol. 22, No. 5, pp. 667-675 (1980).
Tingxian et al., *A Study on Nutritional Characteristics of Rice Straw in China*, Asian-Australasian Journal of Animal Sciences, vol. 6, No. 2, pp. 291-300 (1993).
US Fed News; Dec. 17, 2004; *Optical sensors help farmers find high-quality wheat*; US Fed News.
*Use of near infrared reflectance spectroscopy to Evaluate quality characteristics in whole-wheat grain*; Cozzolino, Daniel, Delucchi, Inés; Kholi, Moham; Vázquez, Daniel, Agricultura Técnica (Chile) 66(4):370-375 (Oct.-Dec. 2006); http://alerce.inia.cl/agriculturatec/Documentos/v.66(04)/NR33788%20p.%20370-375.pdf.
Von Post et al., A High-Throughput DNA Extraction Method for Barley Seed, Euphytica 130: 255-260, 2003.
Weinstock BA, Janni J, Hagen L, Wright S. (2006) Prediction of oil and oleic acid concentrations in individual corn (*Zea mays* L.) kernels using near-infrared reflectance hyperspectral imaging and multivariate analysis. Appl Spectrosc. 60:9-16.
Western Farm Press; Feb. 5, 2005; *Optical Sensors guide to high-quality wheat*; Western Farm Press, p. 7.
Wolf et al., Isolation and Characterization of Zein from Corn Distillers Grain and Related Fractions, Cereal Chemistry, vol. 74, No. 5, 1997, p. 530-536.
Zinn et al, *Flaking corn: Processing Mechanics, Quality Standards, and Impacts on Energy Availability and Performance of Feedlot Cattle*, Journal of Animal Science, 80:1145-1156 (2002).
L. Thylén, P.A. Algerbo, *Development of a Protein Sensor for Combine Harvesters*, http://www.zeltex.com/development_of_a_protein_sensor.doc, (Abstract), printed Jan. 28, 2008, 11 pages.
Gauchi and Chagnon, *Comparison of Selection Methods of Explanatory Variables in PLS Regression with Application to Manufacturing Process Data*, Chemometrics and Intelligent Laboratory Systems, 58 (2001) pp. 171-193.
Guidetti Geri, Viability Myths, <http://waltonfeed.com/self/upack/ag506a1.html>, printed Jun. 21, 2007, 4 pages.
http://asae.frymulti.com/abstract.asp?aid=15195&t=1, Maertans et al., Asabe Technical Library, American Society of Agricultural and Biological Engineers (Abstract), On-Line Measurement of Grain Quality with NIR Technology, Feb. 9-11, 2003, 1 page.
http://asae.frymulti.com/abstract.asp?aid=17856&t=2, Oido et al., Asabe Technical Library, American Society of Agricultural and Biological Engineers (Abstract), A Combine-Mounted NIR Spectroscopy-based Sensor for Single Rice Kernel Protein Content Measurement, published Oct. 7, 2004, 1 page.
http://www.ars.usda.gov/research/publications/publications. htm?SEQ_NO_115+166764, Long, USDA, Agricultural Research Service (Abstract), On-Combine Sensing of Grain Protein Concentration, publication acceptance Jul. 28, 2004, 1 page.
http://www.blackwell-synergy.com/dio/abs/10.1111/j.1439-0523. 2006.01298.x, Montes et al., Blackwell Synergy, Plant Breeding, (Abstract) vol. 125 (6), pp. 591-595, Dec. 2006.
http://www.blackwell-synergy.com/doi/abs.10.1111/j.1439-0523. 2007.01360.x, Montes et al., Blackwell Synergy, Plant Breeding, (Abstract) vol. 126 (3), pp. 329-330, Jun. 2007.
http://www.blackwell-synergy.com/doi/abs.10.1111/j.1439-0523. 2007.01389.x, Montes et al., Blackwell Synergy, Plant Breeding, (Abstract) vol. 126 (5), pp. 521-526, Oct. 2007.
http://www.ethanolproducer.com/article.jsp?article_id=1506, Ethanol Producer Magazine, Zein Protein: Research Could Offset Ethanol Production Costs, Apr. 2002 Issue, 1 page, printed May 21, 2010.
http://www.ingentaconnect.com/content/bsc/pbr/2007/00000126/00000003/art00018;jsessionid=9mc84rjk3t81j.alice?format=print, Montes et al., IngentaConnect, Quality Assessment of Rapeseed Accessions by Means of Near-Infrared Spectroscopy on Combine Harvesters, Plant Breeding, (Abstract) vol. 126 (3), pp. 329-330(2), Jun. 12, 2007.
http://www.meditec.zeiss.com/C125716F004E0776/0/4701250A9FC39862C12571700020D5A6/$File/Innovation_07_10.pdf, Rode et al., Measuring Crop Plant Quality in the Field, 2 pages, printed Feb. 24, 2015.
http://www.sciencedirect.com/science?_ob=ArticleURL&_udi=B6TD1-4PHJH37-2&_user=10&_rdoc=1&_fmt=&_orig=search&_sort=d&view=c&_acct=C000050221&_version=1&_urlVersion=0&_userid=10
&md5=4339128466b4b5c7829c11b65d53dcc6, Montes et al., ScienceDirect, Trends in Plant Science, vol. 12 (10), Novel throughput Phenotyping Platforms in Plant Genetic Studies, pp. 433-436, Oct. 2007.
http://www.sinar.co.uk/products/Crop_protein_nitrogen/accuharvest.asp, Sinar Technology, on Combine Harvester NIR Measurement of Protein, Nitrogen & Moisture in Grain, 2 pages, printed Jan. 28, 2008.
Long et al., *On-Combine Sensing and Mapping of Wheat Protein Concentration*, (USDA-ARS, Columbia Plateau Conservation Research Center, Pendleton, OR 97801); Engel, Richard E.(Land Resources and Environmental Sciences, Montana State University, Bozeman 59501); and Carpenter, Frank M. (Instrument Distributors International, Inc. Gaithersburg, MD 20879), http://www.plantmanagementnetwork.org/pub/cm/research/2005/protein/, 2005, 8 pages.

(56) References Cited

OTHER PUBLICATIONS

P.A. Hailey, Pfizer Central Research, The Role of NIR Spectroscopy in the Measurement of Pharmaceutical Manufacture, http://www.brimrose.com/hailey.html, 9 pages, printed Mar. 27, 2007.
PDK Projects, Inc.: About PDK Projects, http://www.pdkprojects.com/aboutpdk.html 15 pages, printed Dec. 8, 2010.
*Quality sensing at harvest for grain and forage*, Laboratory for Agricultural machinery and Processing, Precision Agriculture, http://www.biw.kuleuven.be/aee/amc/research/precag/projects/yield/quality.htm, 2 pages, printed Dec. 8, 2010.
Brimrose Corporation of America, Baltimore, MD, Luminar 3076 "Seed Meister" NIR Analyzer, http://www.brimrose.com/seed_meister.html, 3 pages, printed Mar. 27, 2007.
Servilla, Welcome to Modern Agriculture, The Journal for Site-Specific Crop Management, *The First Steps to Understanding Agriculture Remote Sensing*, http://www.eomonline.com/modernagsite/archives/Servilla.html, 3 pages, printed Jan. 30, 2008.

\* cited by examiner

US 9,842,252 B2

SYSTEMS AND METHODS FOR USE IN CHARACTERIZING AGRICULTURAL PRODUCTS

CROSS-REFERENCE TO RELATED APPLICATION

This application claims the benefit of U.S. Provisional Application No. 61/182,523, filed on May 29, 2009, the entire disclosure of which is incorporated herein by reference.

FIELD

The present disclosure relates generally to characterizing agricultural products for desired uses, and more particularly to systems and methods for use in characterizing grain products, for example, for optimizing ethanol yield from the grain products.

BACKGROUND

This section provides background information related to the present disclosure which is not necessarily prior art.

Use of alternative energy sources can be desirable for several reasons, for example, reliance on fossil fuel may be decreased, and in turn air pollution may be reduced. And, ethanol production by fermenting carbohydrate-containing plants is one possible source of alternative energy.

SUMMARY

This section provides a general summary of the disclosure, and is not a comprehensive disclosure of its full scope or all of its features.

Example embodiments of the present disclosure generally relate to methods for optimizing ethanol yield from agricultural products. In one example embodiment, a method generally includes imaging agricultural products to determine predicted ethanol yields for the agricultural products, and assigning characterizations to the imaged agricultural products based on their predicted ethanol yields.

Example embodiments of the present disclosure also generally relate to apparatus configured to collect, retain, and/or transport bulk quantities of agricultural products. In one example embodiment, an apparatus generally includes an analyzer configured to image the agricultural products for use in determining predicted ethanol yields for the agricultural products.

Example embodiments of the present disclosure also generally relate to systems for tracking and/or monitoring agricultural products. In one example embodiment, a system generally includes at least one analyzer configured to image the agricultural products for use in determining predicted ethanol yields for the agricultural products, a central processor located remotely from the at least one analyzer and configured to communicate with the at least one analyzer to thereby link the imaged agricultural products with their predicted ethanol yields, and at least one telecommunications link coupling the at least one analyzer to the central processor for allowing the communication between the at least one analyzer and the central processor.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 8:
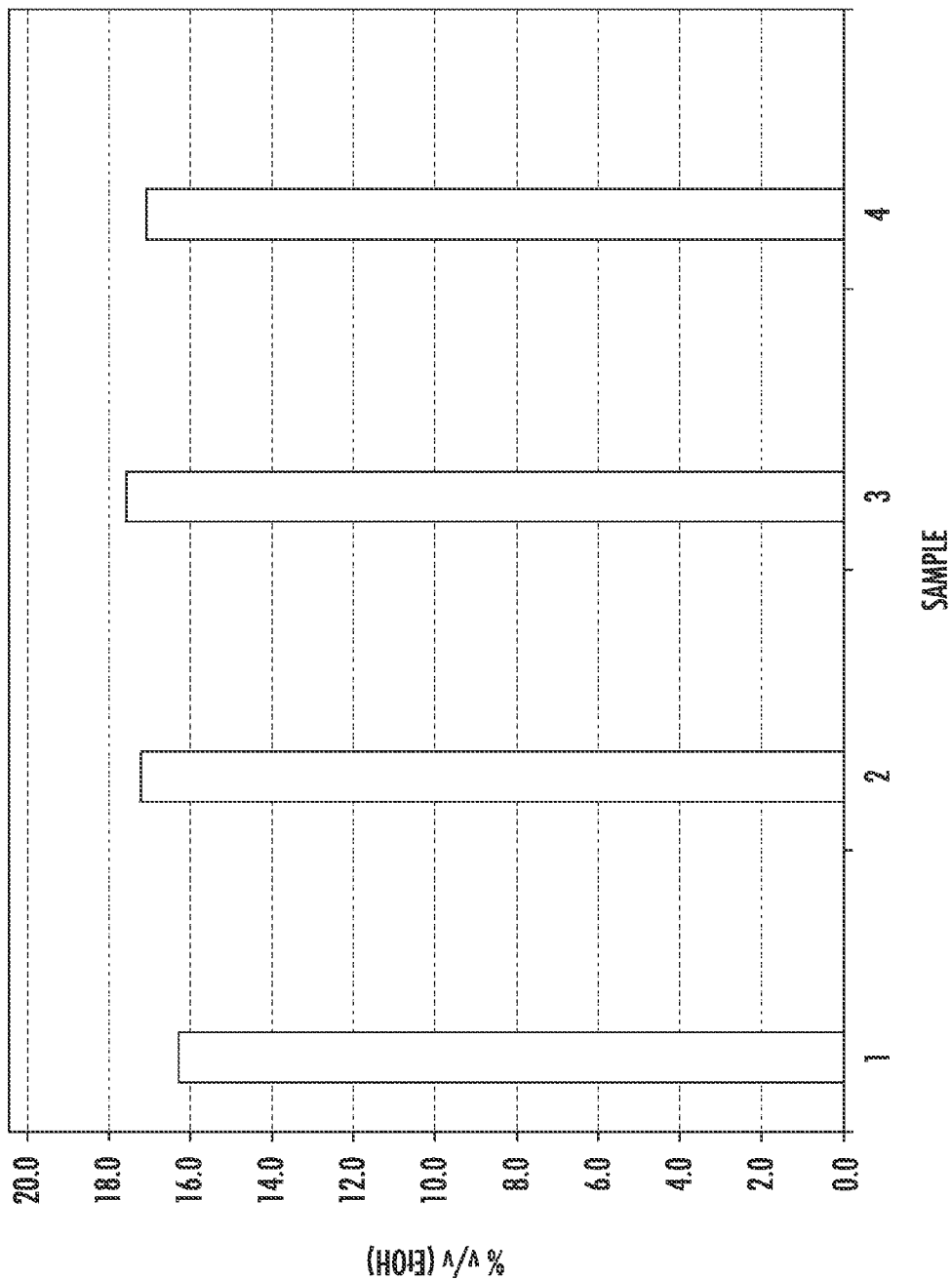
Figure 9:
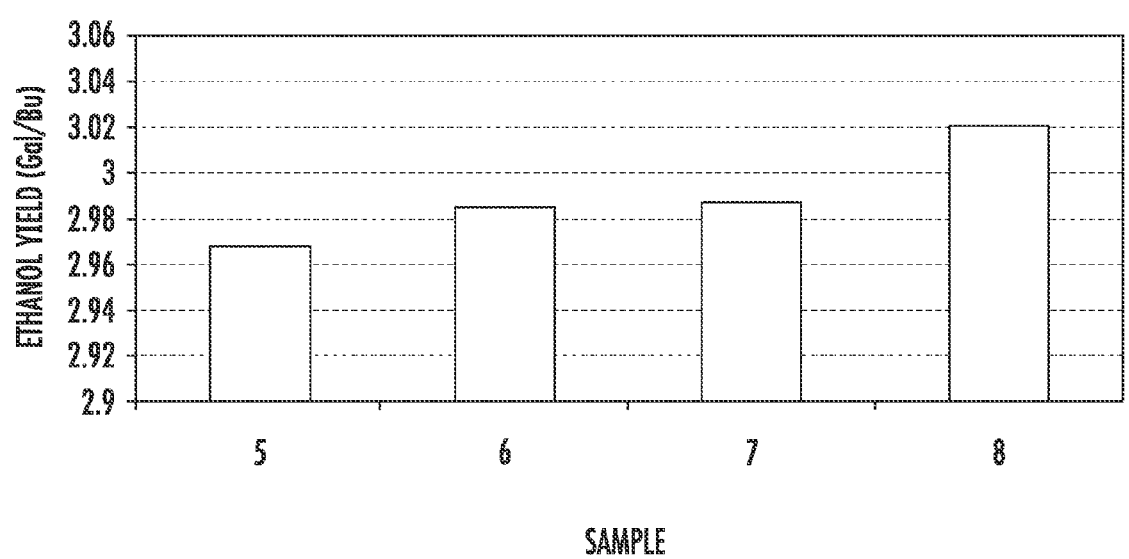

FIG. 8 is an example graph comparing ethanol yield (as expressed in a volume percentage of ethanol) for four corn samples each having a different characterization as determined using near infrared transmittance spectroscopy; and FIG. 9 is an example graph comparing ethanol yield (as expressed in gallons per bushel of ethanol) for four corn samples having different grain grind sizes during fermentation.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper", "remote" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments of the present disclosure generally relate to methods, systems, and apparatus for processing agricultural products and optimizing uses of the agricultural products. For example, agricultural products may be analyzed for traits of interest indicative of optimal uses for the agricultural products (e.g., ethanol production, food production, etc.). This can include determining if and/or confirming that desired traits of interest are present or not present in the agricultural products, and/or comparing analysis results of the agricultural products to known calibration models. Agricultural products having similar desired traits of interest and/or having similarities to known calibration models may be pooled together and then subsequently directed to end users for such optimum uses.

Agricultural products may include, among others, whole grain products, corn, sugarcane, sugar beet, cassava, wheat, barley, rice, rye, oat, sorghum, soybeans, millets, buckwheat, fonio, etc. within the scope of the present disclosure. And, analysis of agricultural products may include analysis of plants, seeds from the plants, plant tissues such as, but not limited to, leafs, flowers, roots, petals, etc. Further, plants may include, for example, an individual plant, more than one plant, a plant variety or hybrid, a crop breed, crop variety, seeds therefrom, etc. within the scope of the present disclosure.

Traits of interest may include, for example, any desirable traits of agricultural products that may enhance production and/or marketability of the agricultural products, etc. Example traits of interest may include, but are not limited to, ethanol yield, digestibility, fermentability to yield ethanol, quality of co-products (e.g., distillers' dried grains with or without solubles, etc.), quality of dry milled products (e.g., corn flour, corn grits, ready-to-eat cereals, brewing adjuncts, extruded and sheeted snacks, breadings, batters, prepared mixes, fortified foods, animal feeds, hominy, corn gluten feed, etc.), quality of industrial products, durability, starch content, protein content, oil content, moisture content, amylase content, starch-protein association, etc. Traits of interest may also include any agronomic, physical, and/or chemical property within the scope of the present disclosure.

Figure 1:
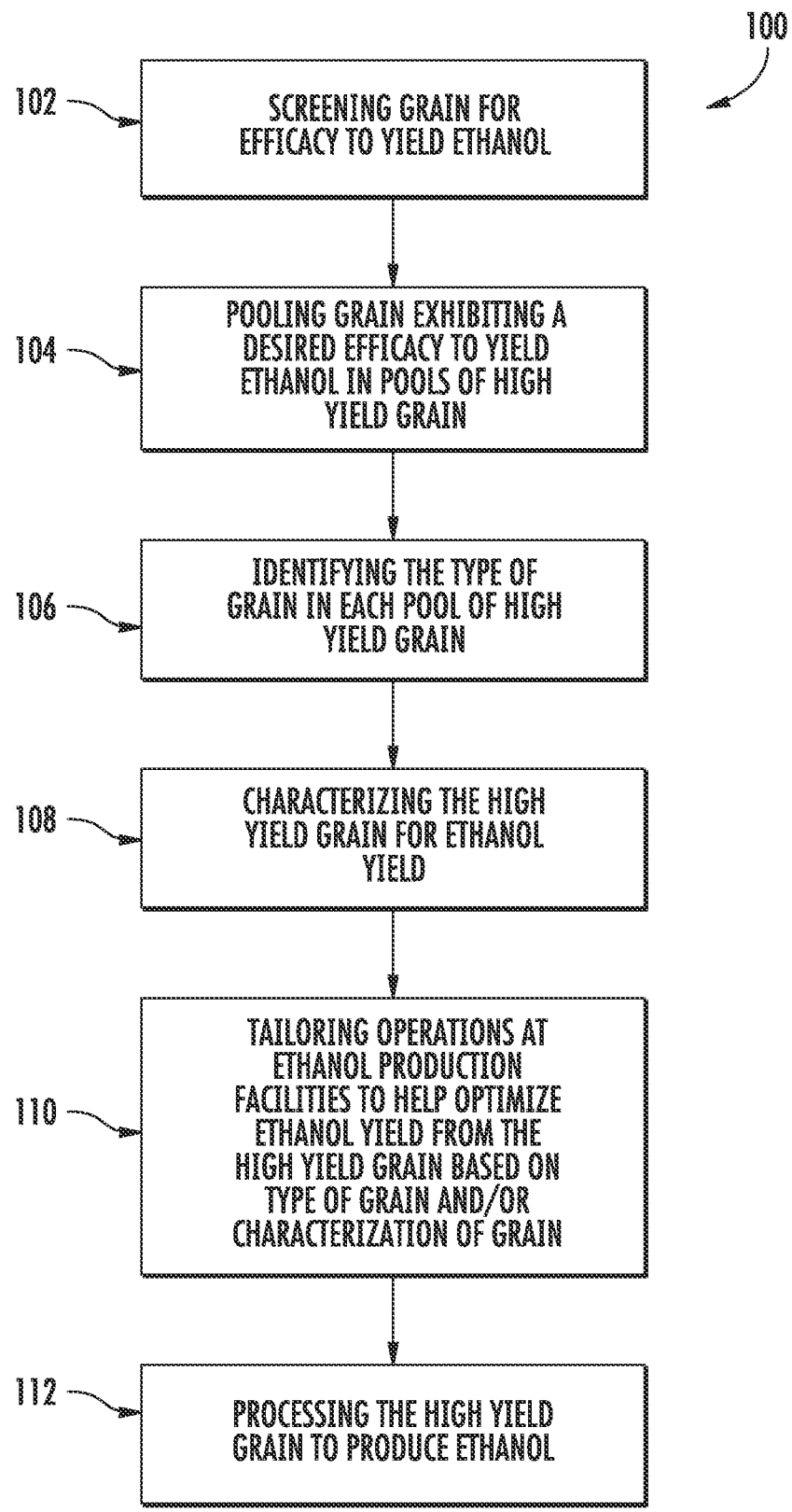
FIG. 1 is a flow chart illustrating an example embodiment of a method for processing grain and optimizing use of the grain to produce ethanol.

With reference now to the drawings, FIG. 1 illustrates an example method (indicated generally at reference number 100) for processing grain (e.g., corn, etc.) and optimizing use of the grain to produce ethanol. As will be described, the illustrated method 100 may facilitate selection of grain having higher ethanol yields for use at ethanol production facilities (e.g., at dry-mill ethanol production facilities, at wet-mill ethanol production facilities, etc.), and may allow for tailoring grain processing operations at the ethanol production facilities to help optimize ethanol yield from the selected grain. As such, the method 100 may help ethanol producers selectively purchase and use (and encourage production of) grain having an efficacy (e.g., grain having at least a minimum desired efficacy, etc.) to yield ethanol, as well as modify grain processing operations to optimize ethanol yield from the selected grain.

As shown in FIG. 1, the illustrated method 100 generally includes initially screening grain for efficacy to yield ethanol (indicated generally at reference number 102). This provides initial separation of grain having an efficacy to yield ethanol from grain not having an efficacy to yield ethanol (as such grain will yield more ethanol per input bushel of grain). The grain screened as having an efficacy to yield ethanol can be qualitatively identified as high yield grain (or high fermentable grain) (e.g., high fermentable corn (HFC), etc.). And, the grain screened as not having an efficacy to yield ethanol can be qualitatively identified as low yield grain (or low fermentable grain) (e.g., low fermentable corn (LFC), etc.). In other example embodiments, grain may be screened for traits of interest other than efficacy to yield ethanol, including, for example, starch content, protein content, oil content, moisture content, etc.

Screening the grain generally includes removing representative samples from the grain (e.g., from bulk quantities of the grain, etc.), and then analyzing the representative samples for presence and/or absence of desired traits of interest as indicators of efficacy to yield ethanol. Different varieties of grain can have distinguishing traits of interest that indicate whether or not the varieties of grain include high yield grain or low yield grain. Screening the representative samples generally includes identifying these distinguishing traits of interest in the representative samples and then determining (based on presence or absence of the distinguishing traits of interest) whether or not the representative samples are high yield grain or low yield grain. The grain from which high yield representative samples where taken is then pooled (e.g., in batches, etc.) (indicated generally at reference number 104). And, desired pools of the high yield grain can then be marked for transport to ethanol production facilities for processing to produce ethanol. The grain from which low yield representative samples where taken is separately pooled and subsequently directed for other uses (e.g., animal feed, etc.).

Any suitable operations for analyzing grain for presence and/or absence of desired traits may be used in connection with screening the grain for efficacy to yield ethanol. As an example, analyzing the grain can include analyzing the grain for fermentability to yield ethanol. As disclosed in U.S. Patent Application Publication Nos. US 2007/0240241 and US 2007/0240242 (both of which are incorporated herein by reference in their entireties), measuring the degree of starch-protein association in grain may be used to predict fermentability of the grain to yield ethanol, as it is believed that lower degrees of starch-protein association are indicative of improved fermentability to yield ethanol. Grain exhibiting a lower degree of starch-protein association, i.e., high fermentable grain, can be separated from grain exhibiting a higher degree of starch-protein association, i.e., low fermentable grain, and pooled, for example, for use at ethanol production facilities.

Screening the grain for efficacy to yield ethanol can take place generally at any time. For example, screening the grain can take place prior to harvesting the grain (e.g., in the field, etc.), during harvesting the grain (e.g., on combines, etc.), after harvesting the grain, while shipping the grain (e.g., on rail cars, on trucks, on barges, etc.), while storing the grain (e.g., at grain elevators, etc.), etc. within the scope of the present disclosure. Typically, though, screening the grain precedes shipping the grain to ethanol production facilities.

With continued reference to FIG. 1, the illustrated method 100 also generally includes identifying the type of grain, for example, by hybrid type, etc., in the pools of high yield grain (indicated generally at reference number 106). This may include, for example, inquiring as to the source of the grain (e.g., the location where the grain was grown; the source of seed from which the grain was grown; the type, brand, etc. of seed from which the grain was grown; etc.), performing physical tests on the grain, performing chemical tests on the grain, etc.

In the illustrated method 100, identifying the type of grain is done after the grain is screened for efficacy to yield ethanol and after the identified high yield grain is pooled. In other example embodiments, identifying the type of grain may be done before the grain is screened for efficacy to yield ethanol, at the same time the grain is screened for efficacy to yield ethanol, or at any other time. In still other example embodiments, identifying the type of grain may be done in lieu of screening the grain for efficacy to yield ethanol. For example, grain may be grown from seeds known to produce high yield grain (e.g., PROCESSOR PREFERRED seed from Monsanto Technology LLC, St. Louis, Mo., etc.). Here, screening the grain for efficacy to yield ethanol may not be required. Instead, identifying the grain as being a type of grain grown from seeds known to produce high yield grain would be sufficient (as such grain could then be marked for transport to ethanol production facilities as described herein).

The illustrated method 100 also generally includes characterizing the pooled high yield grain for ethanol yield (as indicated generally at reference number 108). This can allow ethanol producers to selectively choose high yield grain having desired characterizations (e.g., based on ethanol processing operations at the respective ethanol production facilities, etc.) and reject high yield grain having undesired characterizations. This can also provide initial estimates of ethanol production at the ethanol production facilities (based on the selected high yield grain) for use in managing grain inventory and ethanol output of the facilities. The method 100 may also include characterizing the pooled high yield grain for other traits of interest within the scope of the present disclosure.

Characterizing the grain generally includes removing representative samples from the pools of high yield grain, analyzing the representative samples to determine predicted ethanol yields, and assigning characterizations to the analyzed samples based on their predicted ethanol yields. The characterizations of the representative samples can then be attributed to the pools of grain from which representative samples were taken. Characterizations can include quantitative and/or qualitative identifications within the scope of the present disclosure. For example, grain characterized as having a high ethanol yield may be qualitatively identified as high-high yield grain (e.g., high-high fermentable grain, etc.), and grain characterized as having a low ethanol yield may be qualitatively identified as low-high yield grain (e.g., low-high fermentable grain, etc.). In addition to (or as an alternative to) the "high" and "low" characterizations, grain may also be quantitatively identified using numerical values, ranges, etc. indicative of estimated ethanol yield from the grain when processed at ethanol production facilities.

Grain characterized as having a high ethanol yield may include grain having desired ethanol yields such as, for example, about 2 gallons per bushel or more, about 2.8 gallons per bushel or more, about 3 gallons per bushel or more, etc. However, high yield grain may also (or alternatively) include grain having other ethanol yields within the scope of the present disclosure. Such grain may further be quantitatively identified with a numerical indicator corresponding to the predicted ethanol yield from the grain, for example, 2 (corresponding to an estimated ethanol yield of about 2 gallons per bushel), 2.8 (corresponding to an estimated ethanol yield of about 2.8 gallons per bushel), 3 (corresponding to an estimated ethanol yield of about 3 gallons per bushel), etc.

Any suitable operations for analyzing grain may be used in connection with characterizing grain. For example, analyzing grain may include imaging the representative samples of the grain to obtain spectral images of the representative samples and comparing the spectral images (e.g., calibrated models, spectral curves, etc.) to known images (e.g., calibrated models such as spectral images prepared from similar grains having known and/or calculated (qualitative and/or quantitative) ethanol yields as generated in laboratory calibration tests, etc.) to determine ethanol yields for the representative samples. This generally includes illuminating the representative samples with light and measuring the intensity of light reflected by and/or passing through the samples (e.g., percentages of light reflected by and/or transmitted through the samples, etc.), and then processing the measurements to form the spectral images of the samples. The shapes of the resulting spectral images (which indicate the intensity of the light reflected by and/or transmitted through the sample) are then compared to the known spectral images to thereby characterize the samples (qualitatively and/or quantitatively) based on their relationship to the known spectral curves. In other example embodiments, analyzing grain may include chemically analyzing grain samples (e.g., performing fermentation tests on the grain samples, etc.).

Characterizing the grain for ethanol yield can take place generally at any time. For example, characterizing can take place prior to harvesting the grain (e.g., in the field, etc.), during harvesting the grain (e.g., on combines, etc.), after harvesting the grain, while shipping the grain (e.g., on rail cars, on trucks, on barges, etc.), while storing the grain (e.g., at grain elevators, etc.), at ethanol production facilities (see, e.g., FIG. 2, etc.), etc. within the scope of the present disclosure. In the illustrated embodiment, characterizing the grain generally occurs after the grain is initially screened for efficacy to yield ethanol and/or after the grain type is identified. As such, characterizing operations in the illustrated embodiment are generally directed toward high yield grain (and not low yield grain). And, imaging the grain includes imaging only the screened grain that exhibits an efficacy to yield ethanol.

With continued reference to FIG. 1, the illustrated method 100 also generally includes selecting grain for processing at ethanol production facilities and tailoring operations at the ethanol production facilities (e.g., milling operations, mixing operations, liquefaction operations, cooking operations, fermentation operations, distillation operations, separating operations, steeping operations, etc.) based on the selected type of grain and/or characterization of grain to help optimize ethanol production (indicated generally at reference number 110). For example, both high-high yield grain and low-high yield grain may be selected for processing. Here, the high-high yield grain may be separated from low-high yield grain and processed separately. This may include one or more of fermenting the high-high yield grain and the low-high yield grain for different periods of times; using different combinations of enzymes (e.g., a-amylase, Glucoamylase, etc.), additives (e.g., GC 106 Protease, Vitamin B, yeast nutrient, Fermgen, etc.), etc. with the high-high yield grain and/or the low-high yield grain; using different doses of enzymes, additives, etc. with the high-high yield grain and/or the low-high yield grain, etc. Alternatively, only high-high yield grain may be selected for processing (low-high yield grain may be rejected). The selected grain is then processed to produce ethanol (indicated generally at reference number 112).

In other example embodiments, methods for processing agricultural products may include at least one process other than illustrated in FIG. 1 and/or combinations of processes other than illustrated in FIG. 1. For example, in one example embodiment a method for processing grain is substantially similar to the method 100 previously described and illustrated in FIG. 1, but does not include initially screening the grain for efficacy to yield ethanol. In this example embodiment, the grain is instead characterized for expected ethanol yield (e.g., as high-high yield grain, low-high yield grain, low yield grain, etc.) independent of and without initial screening. Here, characterizing the grain can be viewed as screening the grain and characterizing the grain.

Figure 2:
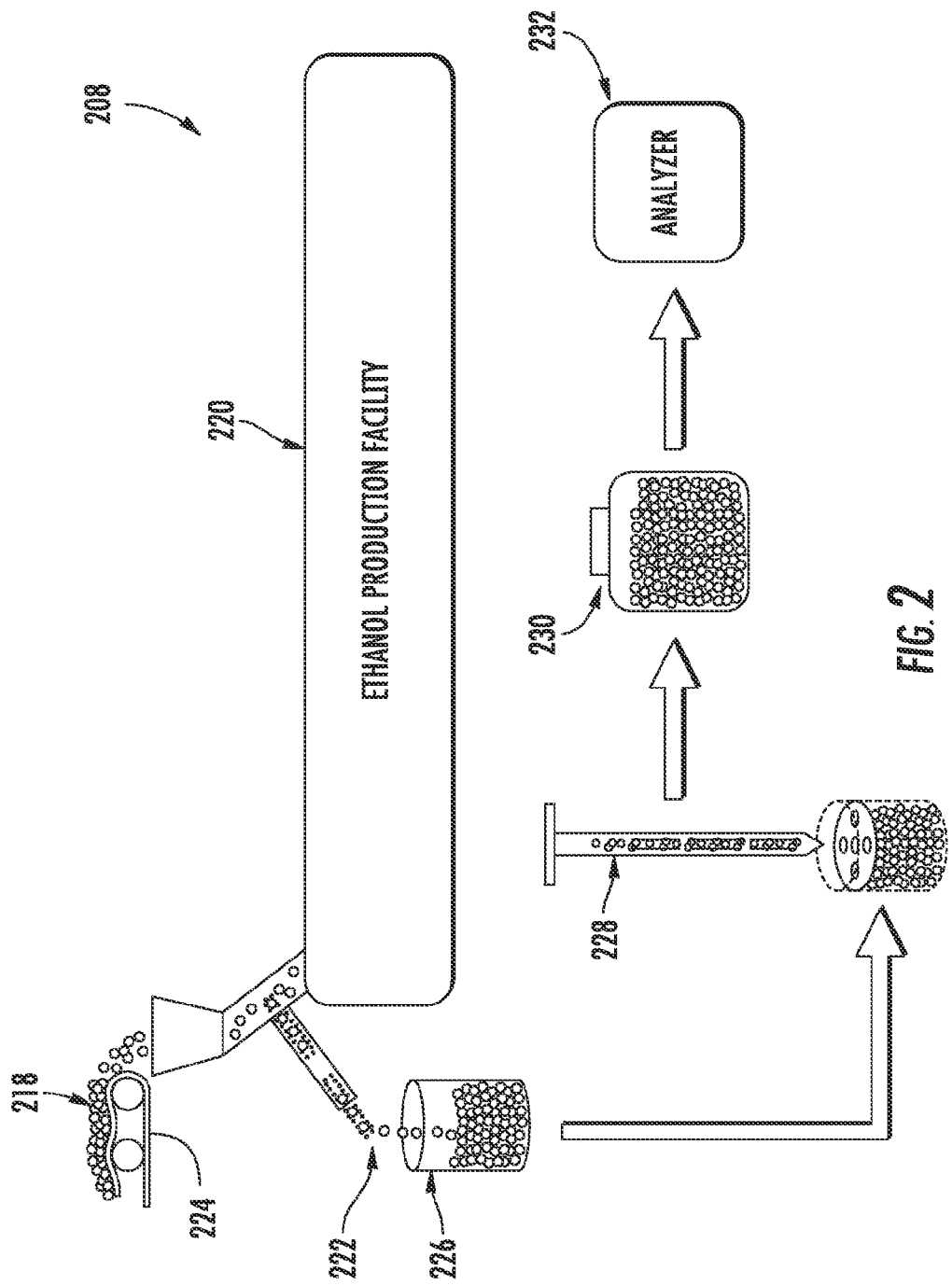
FIG. 2 is a schematic illustrating an example embodiment of an operation for use in characterizing grain received at an ethanol production facility.

FIG. 2 illustrates an example operation generally at reference number 208 for characterizing grain 218 (e.g., grain not initially screened, grain initially screened and pooled as high yield grain, etc.) received at an ethanol production facility 220 for ethanol yield. Here, characterizing the grain generally includes removing representative samples 222 taken from the grain as the grain is delivered to the ethanol production facility on conveyor 224. The representative samples 222 are collected in containers 226. And, once a sufficient sample is collected (e.g., a 60 pound sample, a 70 pound sample, etc.), a core sample is removed from the collected sample (e.g., with a coring device 228, etc.) and transferred to a testing container 230 for analysis (e.g., at analyzer 232, etc.). The sample is then characterized (qualitatively and/or quantitatively) based on results of the analysis. Any suitable analyzer may be used within the scope of the present disclosure including, for example, optical analyzers (e.g., analyzer 332 illustrated in FIG. 3, analyzer 432 illustrated in FIG. 4, optical analyzers available from FOSS (Laurel, Md.), optical analyzers available from NIR Technology Systems (Bankstown, New South Whales, Australia), etc.), chemical analyzers, etc.

In the illustrated embodiment, representative samples 222 are taken from the grain 218 as the grain 218 is delivered to the ethanol production facility 220. In other example embodiments, however, samples can be taken from grain as grain is harvested, prepared for transport, stored, etc. The samples can then be characterized as described herein.

Figure 3:
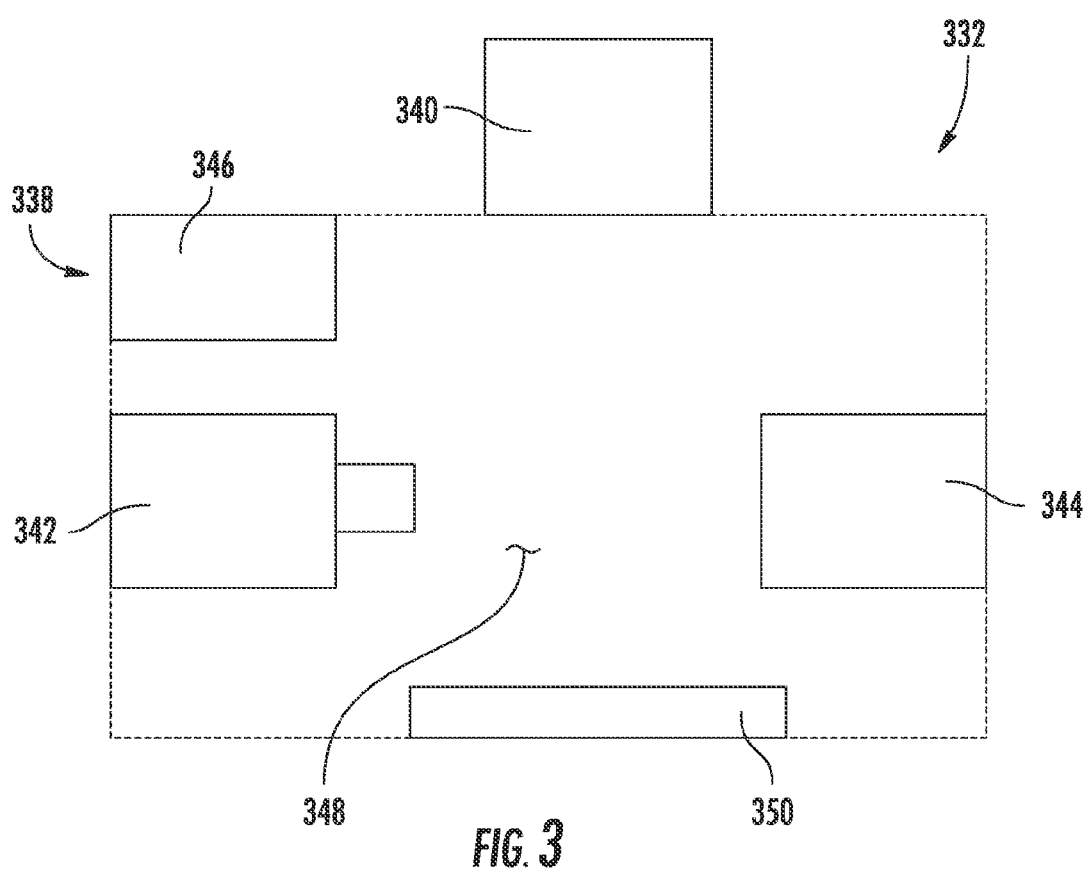
FIG. 3 is a schematic illustrating an example embodiment of an optical analyzer for use in characterizing grain

FIG. 3 illustrates an example embodiment of an optical analyzer 332 for use in characterizing grain within the scope of the present disclosure. The illustrated analyzer 332 uses near infrared transmittance (NIT) spectroscopy for analyzing the grain. This generally includes illuminating representative samples of the grain with light, and measuring the intensity of light passing through the samples in the near infrared spectrum (e.g., over wavelengths ranging from about 860 nanometers to about 1060 nanometers, etc.). The measurements are then processed to form spectral images of the samples indicative of the intensity of the light transmitted through the samples. The shapes of the resulting spectral images are then compared to known spectral images to thereby characterize (qualitatively and/or quantitatively) the samples based on their relationship to the known spectral curves. The characterizations of the representative samples can then be attributed to the grain from which the samples were taken. In other example embodiments, optical analyzers may use methods other than NIT spectroscopy for analyzing grain. For example, optical analyzers may use near infrared reflectance spectroscopy, Fourier transform infrared (FTIR) spectroscopy, etc. for analyzing grain.

The illustrated analyzer 332 generally includes a spectrophotometer 338 for imaging the representative grain samples and a hopper 340 for feeding the samples to the spectrophotometer 338. The hopper 340 is configured (e.g., sized, shaped, constructed, etc.) to receive and hold a desired sample size (e.g., about 500 milliliters, etc.), and then feed the sample to the spectrophotometer 338. The spectrophotometer 338 includes a light source 342 for illuminating the sample and a detector 344 for measuring light transmitted through the illuminated sample. The detector 344 is configured (e.g., sized, shaped, constructed, etc.) to collect spectral images of the sample in the NIR spectrum as the sample moves through the spectrophotometer 338. Any suitable light source (e.g., a tungsten halogen lamp, etc.) can be used for illuminating the sample in the spectrophotometer 338, and any suitable detector (e.g., a silicon photodiode array, etc.) can be used for collecting and/or measuring transmitted light through the sample.

The analyzer 332 may initially be calibrated prior to imaging a representative grain sample in order to provide an accurate comparison of spectral image(s) of the sample to spectral images of grain having calculated and/or known ethanol yields. Such a calibration can be developed by imaging multiple grain samples with the analyzer 332 to measure light transmittance percentages for each of the multiple grain samples, and then analyzing each of the multiple grain samples with traditional chemical methods to determine the qualitative and/or quantitative ethanol yield for each sample. The combination of light transmittance percentages and actual ethanol yield obtained from the multiple samples can then be transformed to calibration constants (e.g., using multiple linear regression techniques, principal components regression techniques, quantitative analysis techniques, quantitative analysis techniques, combinations thereof, etc.). The calibration constants may then be programmed into the analyzer 332 (e.g., using a user interface 346 such as a graphics user interface (GUI), etc. configured to receive data input and/or display data output in connection with operation of the analyzer 332, etc.) for instructing the analyzer 332 to associate certain transmittance percentages of light passing through grain samples with certain qualitative and/or quantitative ethanol yields.

In operation of the calibrated analyzer 332, the hopper 340 is filled with a representative grain sample to be characterized. The sample is fed from the hopper 340 to the spectrophotometer 338 through an optical chamber 348. The light source 342 illuminates the sample as the sample moves through the optical chamber 348, and the detector 344 measures light transmitted through the sample (in the NIR spectrum). The imaged sample is then collected in a tray 350 for removal from the spectrophotometer 338. A processor (not shown) can be included for receiving the light transmittance information from the detector 344 and producing spectral images of the samples. The processor could then compute predicted ethanol yields for the samples based on the spectral images and then assign qualitative and/or quantitative characterizations to the samples based on the predicted ethanol yields. The processor could also be configured to store this information as desired. In some example embodiments, analyzers may be configured to generate multiple spectral images for individual samples fed through the analyzers, and processors of the analyzers may be operable to use an average of the multiple spectral images to compute ethanol yields for the samples. Any suitable processor may be used to evaluate the spectral images within the scope of the present disclosure including, for example, computers, etc.

Figure 4:
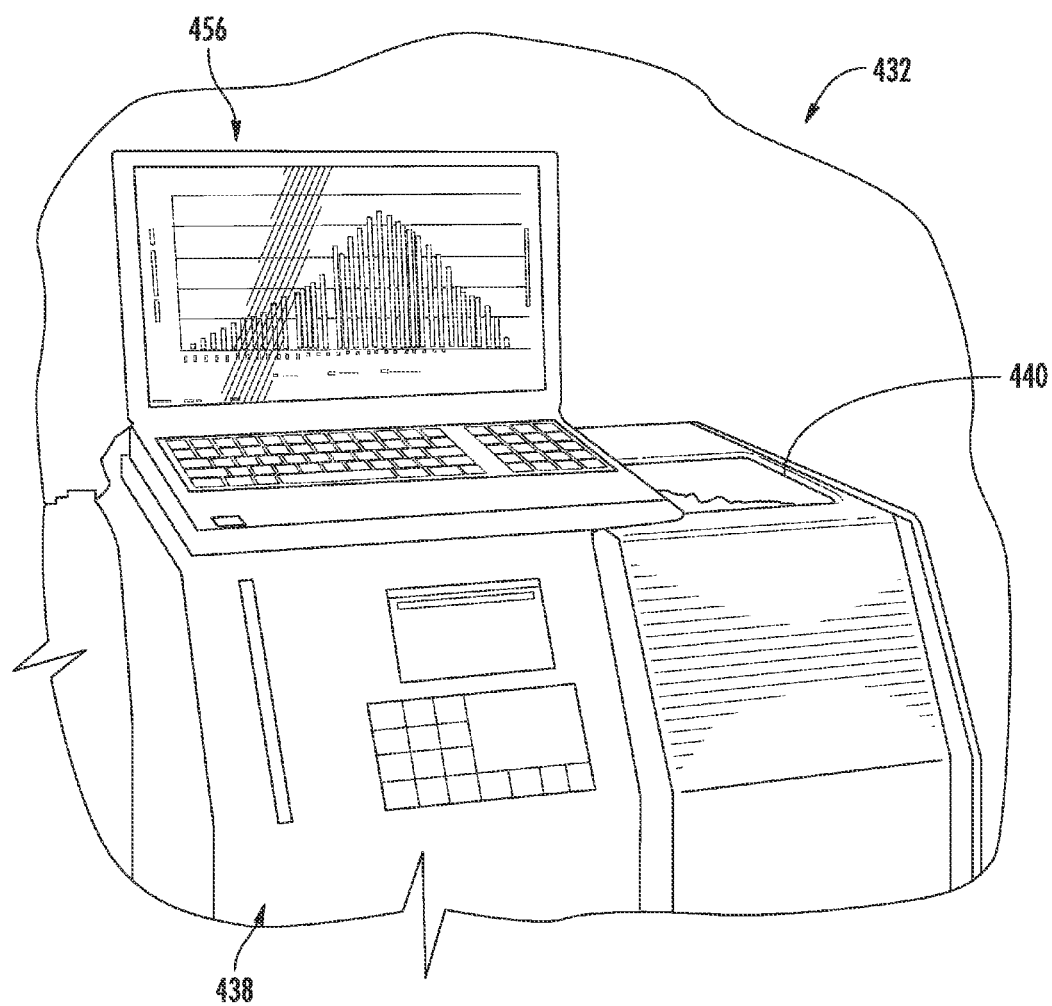
FIG. 4 is a perspective view of another example embodiment of an optical analyzer for use in characterizing grain.

FIG. 4 illustrates another example embodiment of an optical analyzer 432 for use in characterizing grain within the scope of the present disclosure. The illustrated analyzer 432 uses near infrared transmittance (NIT) spectroscopy for analyzing grain and is substantially similar to the analyzer 332 previously described and illustrated in FIG. 3. For example, the illustrated analyzer 432 generally includes a spectrophotometer 438 for imaging the grain in the near infrared (NIR) spectrum (e.g., over wavelengths ranging from about 860 nanometers to about 1060 nanometers, etc.) and a hopper 440 for feeding the grain to the spectrophotometer 438. The analyzer 432 also generally includes a computer 456 (broadly, a processor) coupled to the spectrophotometer 438 for producing spectral images of the grain and computing predicted ethanol yields for the grain based on the spectral images, and then assigning qualitative and/or quantitative characterizations to the grain based on the predicted ethanol yields.

Figure 5:
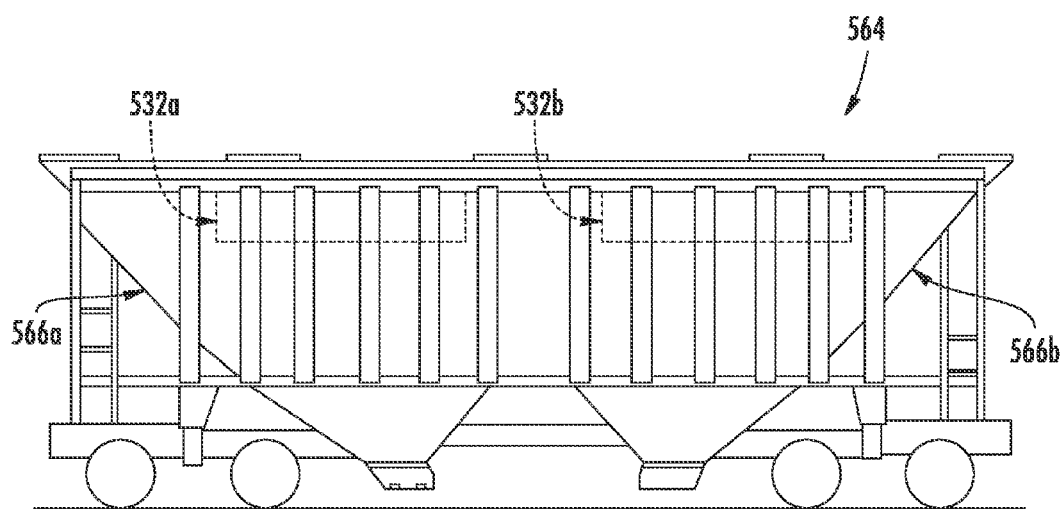
FIG. 5 is a front elevation view of an example embodiment of a rail car having analyzers installed therein for use in characterizing grain on board the rail car.

FIG. 5 illustrates an example embodiment of a rail car 564 for transporting loads of bulk quantities of grain to end users (e.g., ethanol production facilities, etc.). In this example embodiment, analyzers 532a and 532b are installed within the rail car 564 for use in characterizing the loads of grain on board the rail car 564.

As shown in FIG. 5, the illustrated rail car 564 generally includes first and second hoppers 566a and 566b for receiving and storing grain and for transporting the grain as desired on the rail car 564. A first analyzer 532a is installed within the first hopper 566a for use in characterizing the grain in the first hopper 566a, and a second analyzer 532b is installed within the second hopper 566b for use in characterizing the grain in the second hopper 566b. The analyzers 532a and 532b can include any suitable analyzers within the scope of the present disclosure. In the illustrated embodiment, for example, the analyzers 532a and 532b are each optical analyzers (e.g., NIT optical analyzers, etc.) having one or more features of the present disclosure.

In operation of the analyzers 532a and 532b in this example embodiment, grain is deposited into the hoppers 566a and 566b through upper portions of the hoppers 566a and 566b. Light sources (not shown) of the analyzers 532a and 532b (e.g., one or more light sources within each of the hoppers 566a and 566b, etc.) illuminate at least part of the grain as the grain moves into the respective hoppers 566a and 566b, and detectors (not shown) of the analyzers 532a and 532b (e.g., one or more detectors within each of the hoppers 566a and 566b, etc.) measure light transmitted through the illuminated grain. A processor (not shown) receives the light transmittance information from the detectors and produces spectral images of the grain. The processor then computes predicted ethanol yields for the imaged grain in the rail car 564 based on the spectral images and assigns qualitative and/or quantitative characterizations to the grain based on the predicted ethanol yields.

In other example embodiments, analyzers (e.g., optical analyzers, etc.) may be installed to apparatus for handling bulk quantities of grain other than rail cars, for example, combines, other transportation systems (e.g., trailers, barges, etc.), storage units (e.g., grain elevators, etc.), etc. for use in characterizing grain as desired. As such, the analyzers may be used to characterize grain as it is harvested by combines, as it is transported by transportation systems (e.g., trailers, barges, etc.), as it is placed in storage units, etc.

Figure 6:
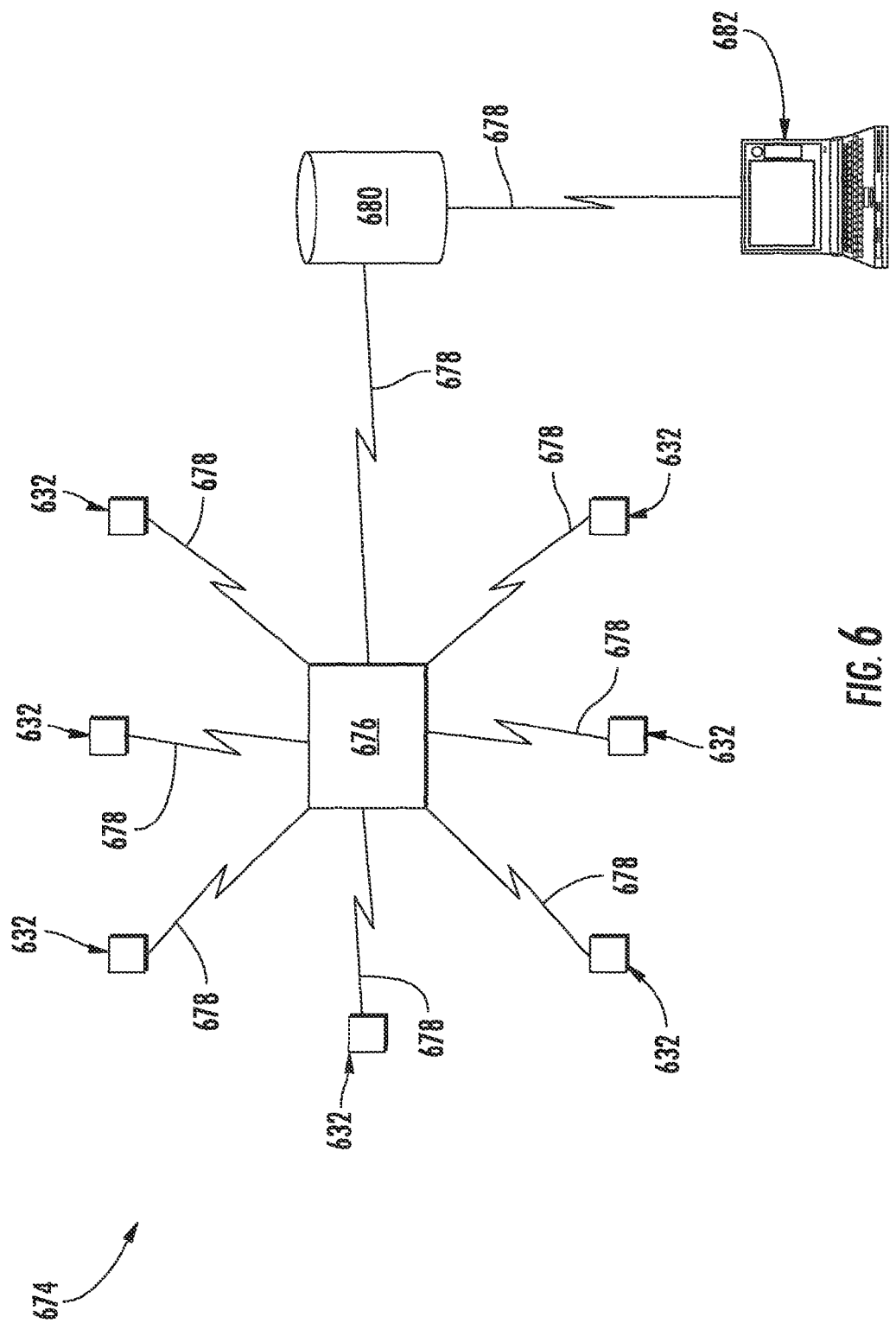
FIG. 6 is a schematic of an example embodiment of a system operable to track pools of grain in accord with one or more aspects of the present disclosure.

FIG. 6 illustrates an example embodiment of a system 674 for tracking pools of grain in accord with one or more aspects of the present disclosure. The system 674 can compile characterization information for analyzed grain and, based on that information, direct grain to end users for optimum use of the grain.

As shown in FIG. 6, the illustrated grain tracking system 674 generally includes multiple analyzers 632 for use in characterizing grain (e.g., in lie of screening the grain, in addition to screening the grain, etc.) and a central processor 676 for processing and storing the characterization information received from the analyzers 632. The analyzers 632 may be located at different desired locations including, for example, farms, on combines, on rail cars, on trucks, at grain elevators, at ethanol production facilities, etc. In addition, one or more of the analyzers 632 may be portable for use in characterizing grain at multiple different locations. For example, the portable analyzer 632 may be used at a first location to characterize grain at the first location, and then transported to a second location to characterize grain at the second location.

The illustrated analyzers 632 are remote devices generally located away from the central processor 676. As such, the analyzers 632 are configured to communicate with the central processor 676 for sending and/or receiving information, for example, relating to characterization of the grain, etc. In the illustrated embodiment, the analyzers 632 are coupled to the central processor 676 by telecommunications links 678 (e.g., hardwired links, phone lines, wireless links, wireless transceivers, network links, internet, intermediary components, etc.). As such, the analyzers 632 can readily communicate characterization information to the central processor 676 to thereby link the characterization information to the respective analyzed pools of grain. The central processor 676 may include any suitable central processor 676 within the scope of the present disclosure, including, for example, one or more computers, etc.

In operation of the illustrated grain tracking system 674, the analyzers 632 operate to initially analyze and characterize pools of grain (e.g., for ethanol yield, total starch, moisture, protein, oil, etc.). The analyzers 632 then communicate the characterization information to the central processor 676. Alternatively, the analyzers 632 may communication image information to the central processor 676 and the central processor 676 may then analyze the image information and characterize the pools of grain. Load tickets can then be generated by the central processor 676 for each analyzed pool of grain identifying, for example, grower identification information, weight, high-yield grain characterization, total starch, moisture, protein, oil, etc. The load tickets may be maintained at a central location, for example, with the central processor 676, or the load tickets may be communicated to the respective analyze 632r for coordination with the respective analyzed pools of grain. The load ticket information may also be transmitted to a network portal server 680 for further analysis (e.g., quality control analysis, for tracking location, etc.), as well as for making the information available to system users (e.g., via a telecommunications link 678 and computer 682, etc.), including ethanol producers, grain suppliers, etc. Through the network portal server 680, the users may be able to search and view available pools of grain and direct desired pools of grain to their desired uses (e.g., ethanol production facilities, etc.).

It should be appreciated that the illustrated grain tracking system 674 can provide a tool for directing loads of high-yield grain to ethanol production facilities for use (e.g., as part of a grain origination control, etc.). As such, ethanol producers can selectively purchase higher yielding grain, grain provided by better suppliers, and/or grain most compatible with their ethanol production operations for subsequent use. Ethanol producers may also be able to identify lower yielding grain suppliers and work with those suppliers to improve their grain quality, for example, by addressing which hybrids the suppliers are using, by evaluating the suppliers' grain drying and storage practices, by offering incentives to the suppliers (e.g., discounts and/or premiums, etc.) to improve grain quality, etc. Moreover, ethanol producers and/or grain suppliers may be able to initially value individual loads of grain (e.g., based on characterization, etc.) and then utilize incentives such as discounts and/or premiums in connection with buying and/or selling those loads (thus providing a more accurate value of different loads of grain).

The grain tracking system 674 can also provide a tool for tracking and/or forecasting ethanol production performance at ethanol production facilities, for example, based on quality of incoming loads of grain (e.g., as part of a quality control, etc.). As such, ethanol producers can track quality of in-bound grain to their ethanol production facilities, tailor operations as necessary, and/or anticipate changes in ethanol yields (which may affect grain purchasing decisions, ethanol output decisions, etc.). In addition, tracking variability in quality of in inbound grain in real time may help reduce variances in ethanol output and may help establish generally consistent ethanol production.

In other example embodiments, grain tracking systems may included one or more components (e.g., analyzers, central processors, etc.) incorporated with software designed for managing grain inventories, grain purchases, etc. for use in streamlining grain processing by allowing rapid, low cost segregation of grains into pools that offer greater value to specific end users. The characterized information associated with each of the individual pools of grain may then be combined with other technologies to monitor the grain during processing in order to modify the processing protocols to create higher value to specific end users such as, for example, ethanol producers.

EXAMPLES

The following examples are merely illustrative, and are not limiting to the disclosure in any way.

Example 1

In this example, flask fermentation experiments (e.g., two liter experiments, etc.) were performed to evaluate effects of various different additives on ethanol yield for various different hybrids of corn. The additives used in this example included GC 106 Protease, Vitamin B, yeast nutrient, and Fermgen. And, the corn hybrids used in this example included MCS 1176, DKC 60-08, and DKC 57-01. For each of the three corn hybrids, seven flask fermentation experiments were performed: (1) a flask fermentation of the respective corn hybrid with no additives (i.e., a control), (2) a flask fermentation of the respective corn hybrid with a one and one-half times does of GC 106 Protease, (3) a flask fermentation of the respective corn hybrid with a single does of Vitamin B, (4) a flask fermentation of the respective corn hybrid with a double dose of Vitamin B, (5) a flask fermentation of the respective corn hybrid with a single does of yeast nutrient, (6) a flask fermentation of the respective corn hybrid with a double does of yeast nutrient, and (7) a flask fermentation of the respective corn hybrid with a single does of Fermgen.

Figure 7:
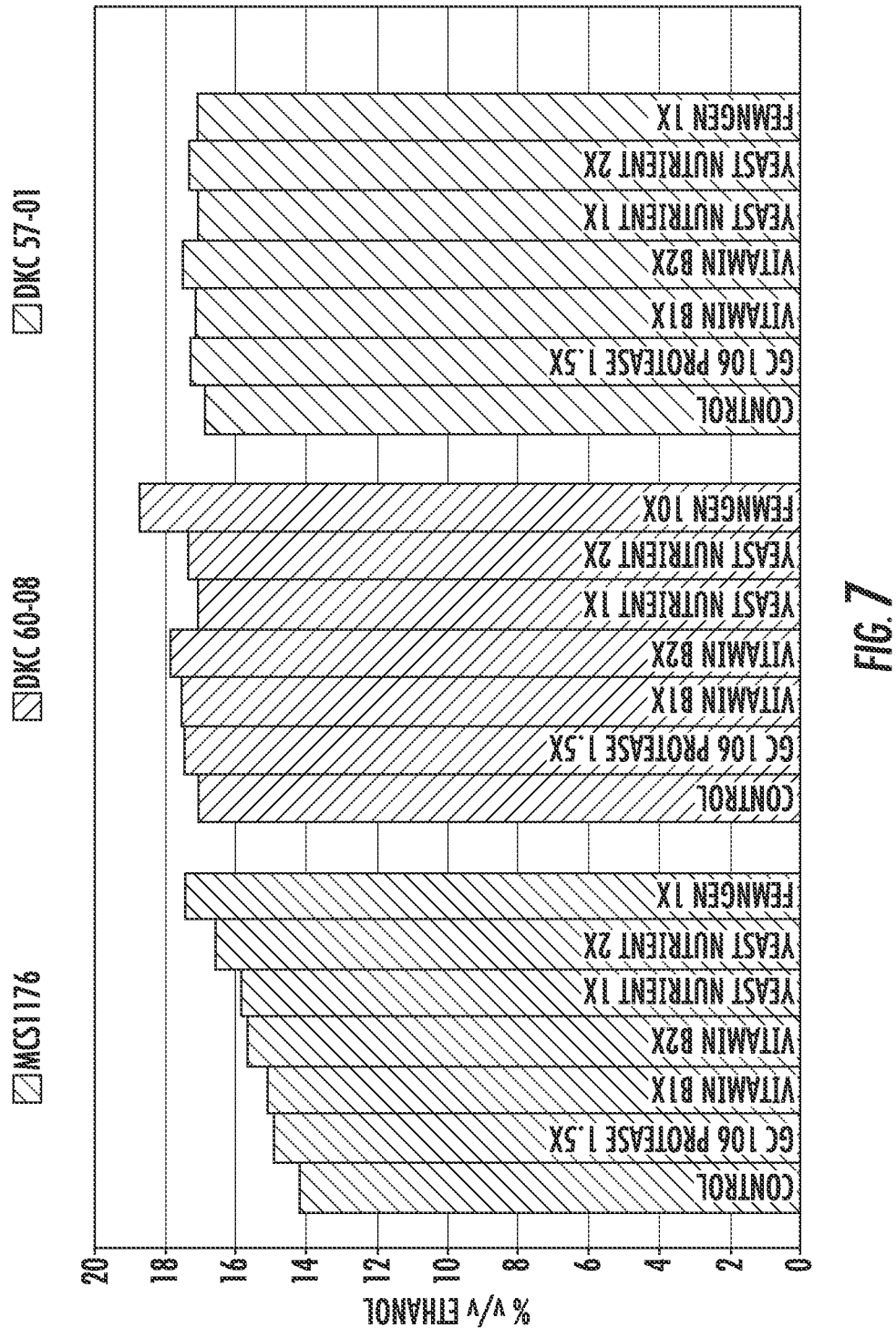
FIG. 7 is an example graph comparing ethanol yield (as expressed in a volume percentage of ethanol) for different corn hybrids having different additives included therewith during fermentation.

FIG. 7 illustrates the results of the seven flask fermentation experiments for each of the three corn hybrids. As shown in FIG. 7, this example suggests that ethanol yield (as expressed in a volume percentage of ethanol) may be improved by additives in certain corn hybrids while not in others.

Example 2

In this example, flask fermentation experiments (e.g., two liter experiments, etc.) were performed to evaluate effects of different Glucoamylase enzyme (GA) dosages on different hybrids of high fermentable corn (HFC) having different qualitative characterizations (e.g., high-HFC and low-HFC, etc.). The corn hybrids used in this example included a generally high-HFC hybrid MCS7693 and a generally low-HFC hybrid MCS 5914. For each of the corn hybrids, a series of flask fermentation experiments were performed using a 0.1 percent dose of GA, a fifty percent increased dose of GA, and a one-hundred percent increased dose of GA. The maximum improvement in yield (as compared to the yield from the experiments using the 0.1 percent dose of GA) was observed when the generally high-HFC hybrid (MCS7693) was dosed with the one-hundred percent increased does of GA. The generally low-HFC hybrid (MCS 5914) did not increase yield in response to the one-hundred percent increased does of GA. Accordingly, this example suggests that ethanol yield may be improved by increasing Glucoamylase enzyme doses in some corn hybrids but not in others.

Example 3

In this example, over one thousand samples of high fermentable corn (HFC) were collected from an ethanol production facility and comparatively analyzed using both NIT optical analysis and flask fermentation analysis. Each of the collected samples were initially analyzed using an optical analyzer operable in the NIT spectrum (e.g., as previously described and illustrated in FIG. 4, etc.) and then quantitatively characterized for ethanol yield. The characterized samples were then divided into four representative samples for comparative flask fermentation. The first representative sample (Sample 1) included the one-hundred fifty samples having the lowest ethanol yield characterizations. The second representative sample (Sample 2) included the one hundred samples having middle range ethanol yield characterizations. The third representative sample (Sample 3) included the one-hundred fifty samples having the highest ethanol yield characterizations. And the fourth representative sample (Sample 4) included a half-and-half mix of the one-hundred fifty samples having the highest ethanol yield characterizations and the one-hundred fifty samples having the lowest ethanol yield characterizations. A representative portion of each of the four representative samples was then fermented until about one percent residual sugars remained.

As shown in FIG. 8, the characterized ethanol yield (as expressed in a volume percentage of ethanol) using NIT optical analysis was directionally consistent with the results of the flask fermentation analysis. For example, flask fermentation of Sample 1 (the samples having the lowest ethanol yield characterizations) yielded about 16.31 percent ethanol (as a volume per volume percentage). Flask fermentation of Sample 2 (the samples having the middle range ethanol yield characterizations) yielded about 17.25 percent ethanol (as a volume per volume percentage). Flask fermentation of Sample 3 (the samples having the highest ethanol yield characterizations) yielded about 17.63 percent ethanol (as a volume per volume percentage). And, flask fermentation of Sample 4 (the samples having the half-and-half mix of the highest ethanol yield characterizations and the lowest ethanol yield characterizations) yielded about 17.14 percent ethanol (as a volume per volume percentage). Thus, the samples having the lowest ethanol yield characterizations had the lowest flask fermentation yield of percent ethanol, and the samples having the highest ethanol yield characterizations had the highest flask fermentation yield of percent ethanol.

Also in this example, different grind sizes of the corn were used during fermentation to evaluate effect on ethanol yield. The one-hundred fifty samples having the lowest ethanol yield characterization were used to prepare two representative samples for flask fermentation, one having a grind size of about 2 millimeters (Sample 5) and one having a grind size of about 0.5 millimeters (Sample 6). And, the one-hundred fifty samples having the highest ethanol yield characterization were used to prepare two representative samples for flask fermentation, one having a grind size of about 2 millimeters (Sample 7) and one having a grind size of about 0.5 millimeters (Sample 8). As shown in FIG. 9, Samples 6 and 8 having the finer grind size showed increases in ethanol production (as expressed in gallons per bushel of ethanol) as compared to respective samples 5 and 7 having the coarser grind size. For example, ethanol production for Sample 5 was about 2.97 gallons per bushel while ethanol production for Sample 6 was abut 2.99 gallons per bushel. And, ethanol production for Sample 7 was about 2.99 gallons per bushel while ethanol production for Sample 8 was about 3.02 gallons per bushel.

In this example, it was also found that drying grain may help increase ethanol yield.

Specific values disclosed herein are exemplary in nature and do not limit the scope of the present disclosure.

The foregoing description of the embodiments has been provided for purposes of illustration and description. It is not intended to be exhaustive or to limit the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A method of sorting agricultural products based on predicted ethanol yield, the method comprising:
   screening harvested agricultural products to determine presence or absence of a trait predictive for ethanol yield;
   identifying the screened agricultural products as at least high yield or low yield according to the determined trait;
   imaging the identified high yield agricultural products and comparing the image to a calibrated model to predict ethanol yield for the agricultural products; and
   sorting the identified high yield agricultural products into at least three pools relating to predicted ethanol yield;
   wherein the at least three pools segregate the sorted agricultural products according to predicted ethanol yield, such that a first one of the at least three pools contains agricultural products with a generally higher predicted ethanol yield, a second one of the at least three pools contains agricultural products with a generally lower predicted ethanol yield, and a third one of the at least three pools contains agricultural products with an intermediate predicted ethanol yield.

2. The method of claim 1, wherein imaging the identified high yield agricultural products includes: generating a spectral image of the agricultural products using near infrared spectroscopy.

3. The method of claim 1, wherein the trait is a qualitative trait.

4. The method of claim 1, further comprising fermenting pools of the sorted agricultural products having a predicted ethanol yield of at least about two gallons per bushel.

5. The method of claim 4, further comprising characterizing the identified high yield agricultural products in each of the at least three pools based on at least one desired trait;
   wherein fermenting the sorted agricultural products includes tailoring at least one ethanol production process based on the at least one desired trait used to characterize the high yield agricultural products to optimize ethanol yield from the agricultural products.

6. The method of claim 5, wherein tailoring the at least one ethanol production process includes combining at least one additive with the agricultural products during at least one ethanol production process.

7. The method of claim 6, wherein the at least one additive includes an enzyme.

8. The method of claim 5, wherein tailoring the at least one ethanol production process includes combining at least two additives with the agricultural products during at least one ethanol production process, and wherein at least one of the at least two additives is an enzyme.

9. The method of claim 4, further comprising, prior to fermenting pools of the sorted agricultural products:
   drying the sorted agricultural products; and
   grinding the dried agricultural products to a grind size of about 500 μm.

10. The method of claim 9, wherein the trait predictive for ethanol yield is degree of starch-protein association.

11. The method of claim 1, further comprising quantitatively identifying ones of the at least three pools of the sorted agricultural products that have a predicted ethanol yield of at least about two gallons per bushel with a numerical indicator corresponding to the predicted ethanol yield for the agricultural product.

12. The method of claim 11, further comprising quantitatively identifying pools of the sorted agricultural products that have a predicted ethanol yield of at least about 2.8 gallons per bushel with a numerical indicator corresponding to the predicted ethanol yield of at least about 2.8 gallons per bushel.

13. The method of claim 12, further comprising quantitatively identifying pools of the sorted agricultural products that have a predicted ethanol yield of at least about three gallons per bushel with a numerical indicator corresponding to the predicted ethanol yield of at least about three gallons per bushel.

14. The method of claim 1, wherein the agricultural products include at least one of whole grain agricultural products, corn, sugarcane, sugar beet, and cassava.

15. The method of claim 1, wherein imaging the agricultural products occurs while transporting the agricultural products.

16. The method of claim 15, wherein imaging the agricultural products occurs on a rail car.

17. The method of claim 1, wherein imaging the agricultural products occurs while storing the agricultural products.

18. The method of claim 1, further comprising: collecting representative samples of the identified high yield agricultural products; and removing a core sample from each of the collected representative samples; wherein imaging the identified high yield agricultural products includes imaging the core samples.

19. The method of claim 1, wherein the trait is a quantitative trait.

20. The method of claim 1, further comprising:
drying the sorted agricultural products in at least one of the at least three pools; and
grinding the dried agricultural products to a grind size of about 500 µm.

21. The method of claim 1, wherein the trait predictive for ethanol yield is degree of starch-protein association.

22. The method of claim 1, further comprising characterizing the identified high yield agricultural products in each of the at least three pools based on at least one desired trait, whereby a decision to select agricultural products from ones of the at least three pools can be based, at least in part, on the associated characterization.

23. The method of claim 22, further comprising quantitatively identifying each of the at least three pools of the sorted agricultural products based on the ethanol yield of the agricultural products included in the pools.

24. The method of claim 1, further comprising harvesting the agricultural products.

* * * * *